(12) United States Patent
Endo

(10) Patent No.: US 11,044,416 B2
(45) Date of Patent: Jun. 22, 2021

(54) ENDOSCOPE SYSTEM, PROCESSOR DEVICE, AND ENDOSCOPE SYSTEM OPERATION METHOD

(71) Applicant: FUJIFILM Corporation, Tokyo (JP)

(72) Inventor: Maiko Endo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 80 days.

(21) Appl. No.: 16/161,064

(22) Filed: Oct. 16, 2018

(65) Prior Publication Data

US 2019/0082094 A1    Mar. 14, 2019

Related U.S. Application Data

(63) Continuation-in-part of application No. PCT/JP2017/008862, filed on Mar. 7, 2017.

(30) Foreign Application Priority Data

Apr. 21, 2016   (JP) .............................. JP2016-085335

(51) Int. Cl.
H04N 5/235 (2006.01)
H04N 9/04 (2006.01)
(Continued)

(52) U.S. Cl.
CPC ....... *H04N 5/2357* (2013.01); *A61B 1/00006* (2013.01); *A61B 1/00009* (2013.01);
(Continued)

(58) Field of Classification Search
CPC . A61B 1/00006; A61B 1/00009; A61B 1/043; A61B 1/045; A61B 1/06;
(Continued)

(56) References Cited

U.S. PATENT DOCUMENTS

2003/0060684 A1* 3/2003 Ayame ............... A61B 1/00096
600/181
2004/0267091 A1  12/2004 Imaizumi et al.
(Continued)

FOREIGN PATENT DOCUMENTS

JP    2005006768    1/2005
JP    2011183055    9/2011
(Continued)

OTHER PUBLICATIONS

"Search Report of Europe Counterpart Application", dated Apr. 29, 2019, p. 1-p. 9.
(Continued)

*Primary Examiner* — Joon Kwon
(74) *Attorney, Agent, or Firm* — JCIPRNET

(57) ABSTRACT

Provided are an endoscope system, a processor device, and an endoscope system operation method capable of adjusting an exposure amount with higher accuracy than in the related art. An endoscope system includes a light source unit that emits illumination light, an image sensor that images an observation target by using the illumination light, an image acquisition unit that acquires plural-color images obtained by imaging the observation target by using the image sensor, and an exposure amount control portion that controls an exposure amount in a case where the image acquisition unit obtains the plural-color images, by using some-color images among the plural-color images.

19 Claims, 10 Drawing Sheets

(51) Int. Cl.
*A61B 1/06* (2006.01)
*A61B 1/045* (2006.01)
*A61B 1/00* (2006.01)
*G02B 23/24* (2006.01)
*A61B 1/04* (2006.01)
*A61B 5/00* (2006.01)

(52) U.S. Cl.
CPC .............. *A61B 1/043* (2013.01); *A61B 1/045* (2013.01); *A61B 1/06* (2013.01); *A61B 1/0638* (2013.01); *A61B 5/0084* (2013.01); *G02B 23/2461* (2013.01); *G02B 23/2484* (2013.01); *H04N 5/2352* (2013.01); *H04N 9/0451* (2018.08); *A61B 5/0075* (2013.01); *A61B 5/0077* (2013.01); *A61B 2505/05* (2013.01); *H04N 5/2353* (2013.01); *H04N 5/2354* (2013.01); *H04N 2209/047* (2013.01)

(58) Field of Classification Search
CPC . A61B 1/0638; A61B 2505/05; A61B 5/0075; A61B 5/0077; A61B 5/0084; G02B 23/2461; G02B 23/2484; G06T 7/12; H04N 2209/047; H04N 5/2352; H04N 5/2353; H04N 5/2354; H04N 5/2357; H04N 9/0451
See application file for complete search history.

(56) References Cited

U.S. PATENT DOCUMENTS

| | | | | |
|---|---|---|---|---|
| 2005/0251230 A1* | 11/2005 | MacKinnon | ......... | A61B 1/0638 607/88 |
| 2007/0073104 A1* | 3/2007 | Iketani | ................. | A61B 1/042 600/109 |
| 2012/0075449 A1* | 3/2012 | Yasuda | ................ | A61B 1/0638 348/68 |
| 2013/0245410 A1 | 9/2013 | Saito | | |
| 2014/0046131 A1 | 2/2014 | Morita et al. | | |
| 2014/0092226 A1 | 4/2014 | Kuriyama | | |
| 2014/0192551 A1 | 7/2014 | Masaki | | |

FOREIGN PATENT DOCUMENTS

| | | |
|---|---|---|
| JP | 2013188365 | 9/2013 |
| JP | 2014033777 | 2/2014 |
| JP | 2015036066 | 2/2015 |
| WO | 2014045647 | 3/2014 |
| WO | 2014156604 | 10/2014 |

OTHER PUBLICATIONS

"Office Action of Japan Counterpart Application," with English translation thereof, dated Oct. 29, 2019, p. 1-p. 8.

"International Preliminary Report on Patentability (Form PCT/IPEA/409) of PCT/JP2017/008862," dated Feb. 16, 2018, with English translation thereof, pp. 1-19.

"International Search Report (Form PCT/ISA/210) of PCT/JP2017/008862," dated Jun. 6, 2017, with English translation thereof, pp. 1-5.

"Office Action of Japan Counterpart Application", dated Jun. 9, 2020, with English translation thereof, p. 1-p. 8.

"Office Action of Europe Counterpart Application", dated Jun. 2, 2020, p. 1-p. 4.

* cited by examiner

ENDOSCOPE SYSTEM, PROCESSOR DEVICE, AND ENDOSCOPE SYSTEM OPERATION METHOD

CROSS-REFERENCE TO RELATED APPLICATIONS

This application is a Continuation-in-part of PCT International Application No. PCT/JP2017/008862 filed on Mar. 7, 2017, which claims priority under 35 U.S.C § 119(a) to Japanese Patent Application No. 2016-085335 filed on Apr. 21, 2016. Each of the above application(s) is hereby expressly incorporated by reference, in its entirety, into the present, application.

BACKGROUND OF THE INVENTION

1. Field of the Invention

The present invention relates to an endoscope system, a processor device, and an endoscope system operation method capable of automatically adjusting an exposure amount when an observation target is imaged.

2. Description of the Related Art

In a medical field, generally, diagnosis is performed by using an endoscope system including a light source device, an endoscope, and a processor device. The light source device generates, for example, white light as illumination light. The endoscope images an observation target irradiated with the illumination light. The processor device generates and displays an image (hereinafter, referred to as an observation image) for observation displayed on a monitor by using an image (hereinafter, referred to as a captured image) obtained by imaging the observation target with the endoscope.

In a case where an amount of illumination light is set to be constant at all times, an exposure amount in an image sensor changes depending on a relative distance or angle between a tip end portion of the endoscope and the observation target, and thus the brightness of the observation image is not stable. Thus, in the endoscope system, typically, an exposure amount in the image sensor is made substantially constant even in a case where a relative distance or angle between the tip end portion of the endoscope and the observation target changes, by automatically adjusting an amount of illumination light. Consequently, the endoscope system can image an observation target at the substantially identical brightness at all times.

For example, there is an endoscope system in which an observation target is sequentially imaged by using red light (hereinafter, referred to as R light), green light (hereinafter, referred to as G light), and blue light (hereinafter, referred to as B light), and thus a red image (hereinafter, referred to as an R image), a green image (hereinafter, referred to as a G image), and a blue image (hereinafter, referred to as a B image) are acquired. In such an endoscope system, an exposure amount adjustment method is known in which the brightness of each color image is weighted, and thus an exposure amount in the next imaging is adjusted (JP2014-033777A).

In an endoscope system in which moving images in a plurality of modes in which illumination light to be used differs are simultaneously displayed, a method is known in which exposure amounts for capturing other moving images are interlocked with an exposure amount for capturing a single moving image used as a reference, so as to be automatically determined (JP2013-188365A).

SUMMARY OF THE INVENTION

In an endoscope system of the related art, an exposure amount is automatically adjusted such that the brightness of an observation image is stabilized, but there is still a case where a doctor or the like who is a user of the endoscope system feels a change (so-called "flickering") in the brightness of an observation image. Thus, it is necessary to adjust an exposure amount with higher accuracy.

For example, in the endoscope system of the related art, three-color captured images such as an R image, a G image, and a B image are simultaneously or sequentially acquired, and an observation image having a natural shade is generated and displayed. An exposure amount in the next imaging is determined by using the brightness or the like of the observation image.

However, in an observation image, for example, a blood vessel appears more darkly than the mucous membrane. Thus, since an observation image in which a blood vessel appears favorably is darker than an observation image in which the blood vessel does not appear much, in a case where an exposure amount in the next imaging is determined by using the observation image in which the blood vessel appears favorably, an exposure amount may be adjusted to be too large. In contrast, in a case where an exposure amount in the next imaging is determined by using the observation image in which the blood vessel does not appear much, an exposure amount may be adjusted to be too small. Thus, in the endoscope system of the related art, although an exposure amount is automatically adjusted, a change in the brightness of an observation image may not be negligible.

An object of the present invention is to provide an endoscope system, a processor device, and an endoscope system operation method capable of adjusting an exposure amount with higher accuracy than in the related art.

According to an aspect of the present invention, there is provided an endoscope system comprising a light source unit that emits illumination light; an image sensor that images an observation target by using the illumination light; an image acquisition unit that acquires plural-color images obtained by imaging the observation target by using the image sensor; and an exposure amount control portion that controls an exposure amount in a case where the image acquisition unit obtains the plural-color images, by using some-color images among the plural-color images.

The endoscope system preferably further comprises a light source control unit that controls an amount, a wavelength range, or an optical spectrum of the illumination light emitted from the light source unit, and the exposure amount control portion preferably calculates an exposure amount in a case where the image acquisition unit obtains the plural-color images, by using some-color images of the plural-color images, outputs the calculated exposure amount to the light source control unit, and controls an exposure amount.

The exposure amount control portion preferably controls an exposure amount by using a color image in which a change of a pixel value is smallest in a case where an angle of view is changed among the plural-color images.

The exposure amount control portion preferably controls an exposure amount by using a color image in which the smallest light absorption occurs in blood among the plural-color images.

The exposure amount control portion preferably controls an exposure amount by using a color image in which a wavelength range is 460 nm or more and 700 nm or less among the plural-color images.

The exposure amount control portion preferably controls an exposure amount by using a color image in which the smallest light absorption occurs in a yellow pigment among the plural-color images.

The exposure amount control portion preferably controls an exposure amount by using a color image in which a wavelength range is 525 nm or more and 700 nm or less among the plural-color images.

The exposure amount control portion preferably controls an exposure amount by using a color image in which the smallest light absorption occurs in a pigment used for endoscope observation among the plural-color images.

The exposure amount control portion preferably controls an exposure amount by setting an amount, a wavelength range, or an optical spectrum of light included in the illumination light.

The exposure amount control portion controls an exposure amount by setting an exposure time of the image sensor.

The exposure amount control portion uses the plural-color images which are weighted for control of an exposure amount, and controls an exposure amount by setting weights of some-color images of the plural-color images to be larger than weights of the other-color images.

The endoscope system preferably further comprises a region detection unit that detects a region to be used for control of an exposure amount from the plural-color images, and the exposure amount control portion preferably controls an exposure amount by using the region detected by the region detection unit.

The endoscope system preferably further comprises an observation condition determination unit that determines an observation condition by using one or more of the plural-color images, and the exposure amount control portion preferably selects an image to be used for control of an exposure amount from among the plural-color images by using the observation condition.

The observation condition determination unit preferably determines an observation distance as the observation condition.

The observation condition determination unit preferably determines an observation part as the observation condition.

According to another aspect of the present invention, there is provided a processor device comprising an image acquisition unit that acquires plural-color images from an image sensor which images an observation target by using illumination light; and an exposure amount control portion that controls an exposure amount in a case where the image acquisition unit obtains the plural-color images, by using some-color images of the plural-color images.

According to still another aspect of the present invention, there is provided an endoscope system operation method comprising a step of causing a light source unit to emit illumination light; a step of causing an image sensor to image an observation target by using the illumination light; a step of causing an image acquisition unit to acquire plural-color images obtained by imaging the observation target by using the image sensor; and a step of causing an exposure amount control portion to controls an exposure amount in a case where the image acquisition unit obtains the plural-color images, by using some-color images among the plural-color images.

According to the present invention, since an exposure amount in a case where the image acquisition unit obtains the plural-color images is controlled by using some-color images among plural-color images, it is possible to provide an endoscope system, a processor device, and an endoscope system operation method capable of adjusting an exposure amount with higher accuracy than in the related art.

DESCRIPTION OF THE PREFERRED EMBODIMENTS

First Embodiment

Figure 1:
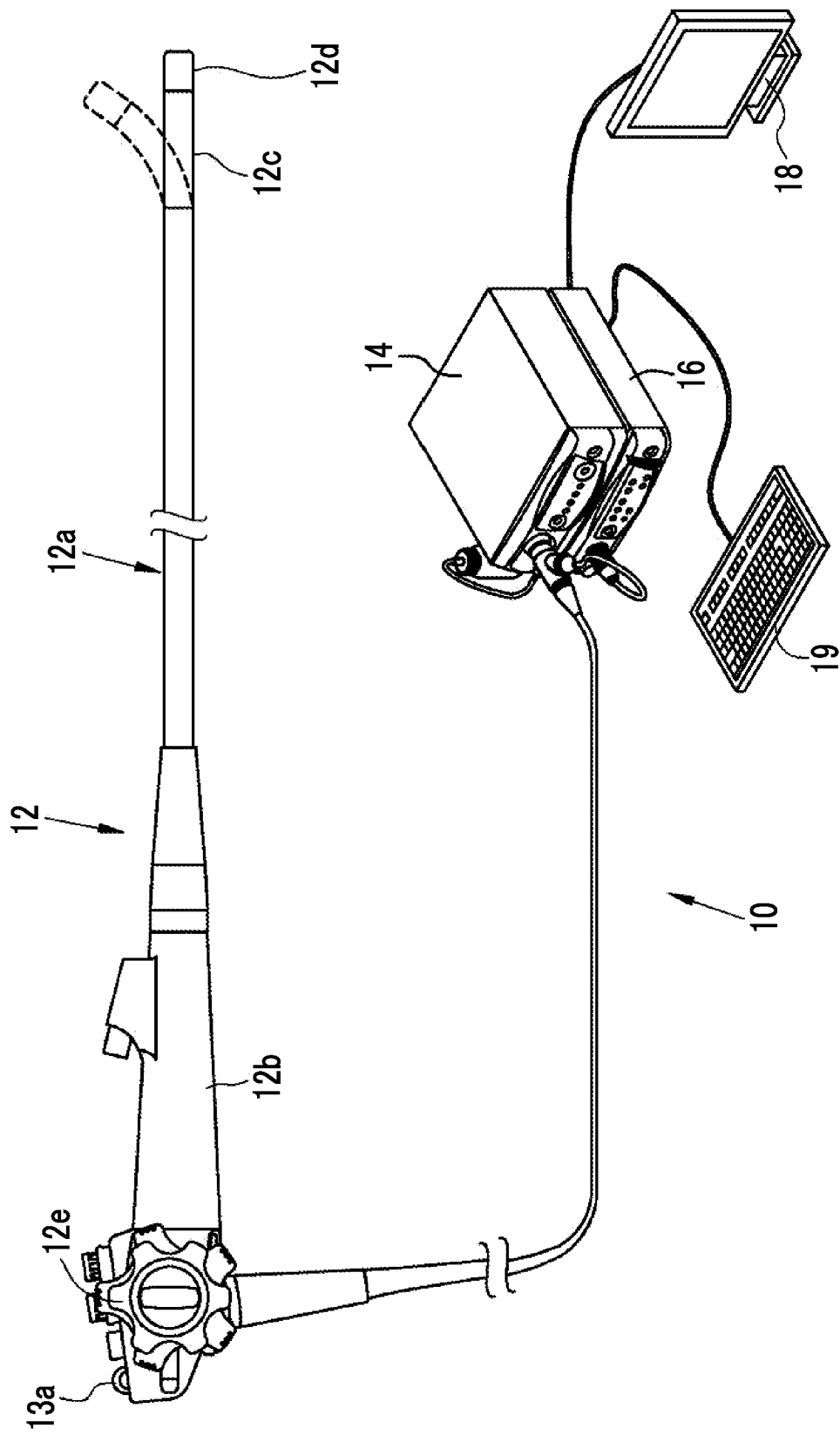
FIG. 1 is an exterior diagram of an endoscope system.

As illustrated in FIG. 1, an endoscope system 10 includes an endoscope 12 which images an observation target, a light source device 14, a processor device 16, a monitor 18 which is a display unit, and a console 19. The endoscope 12 is optically connected to the light source device 14, and is also electrically connected to the processor device 16. The endoscope 12 has an insertion portion 12a inserted into a subject, an operation portion 12b provided at a basal end portion of the insertion portion 12a, a curved portion 12c provided on a distal end side of the insertion portion 12a, and a tip end portion 12d. The curved portion 12c is curved by operating an angle knob 12e of the operation portion 12b. As a result of the curved portion 12c being curved, the tip end portion 12d is directed in a desired direction. The tip end portion 12d is provided with an injection port (not illustrated) for injecting air or water toward an observation target. The operation portion 12b is provided with a zoom operation portion 13a in addition to the angle knob 12e.

The processor device 16 is electrically connected to the monitor 18 and the console 19. The monitor 18 outputs and displays an observation image in each observation mode and image information or the like attached to the observation image as necessary. The console 19 functions as a user interface receiving an input operation such as function setting. The processor device 16 may be connected to an externally attached recording unit (not illustrated) which records an image, image information, or the like.

Figure 2:
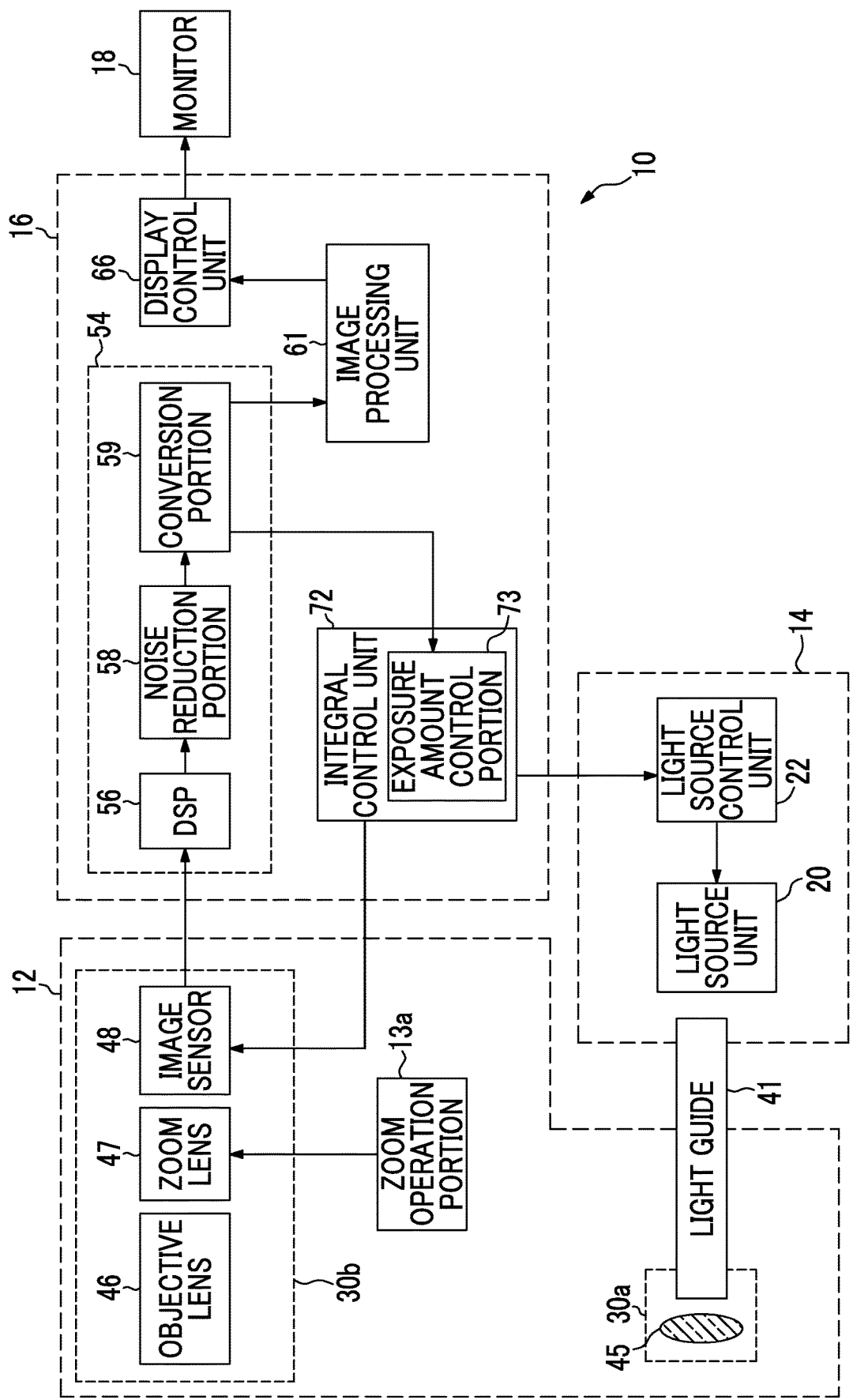
FIG. 2 is a block diagram of the endoscope system.

As illustrated in FIG. 2, the light source device 14 includes a light source unit 20 which emits illumination light, and a light source control unit 22 which controls driving of the light source unit 20.

The light source unit 20 includes, for example, a red light source emitting R light, a green light source emitting G light, and a blue light source emitting B light. Each of the light sources of the respective colors is, for example, a semiconductor light source such as a light emitting diode (LED), and a light amount and a light emission timing thereof may be separately controlled. The light source unit 20 may emit white light formed of R light, G light, and B light, by substantially simultaneously lighting the red light source, the green light source, and the blue light source. The term "substantially simultaneously" indicates that red light source, the green light source, and the blue light source are lighted or emit light within one identical imaging timing (hereinafter, referred to as an imaging frame) in an image sensor 48. For example, even in a case where the red light source, the green light source, and the blue light source are sequentially lighted while the image sensor 48 images an observation target once, R light, G light, and B light emitted therefrom are used in one identical imaging, and thus lighting timings of the red light source, the green light source, and the blue light source are substantially the same as each other, and emission of the R light, the G light, and the B light are substantially simultaneously performed.

The light source unit 20 mixes light beams emitted from the respective light sources with each other by using mirrors or prisms (not illustrated) (including a dichroic mirror or a dichroic prism transmitting or reflecting some components in a wavelength range). The configuration of the light source unit 20 of the present embodiment is only an example, and the light source unit 20 may have any configuration as long as a plurality of kinds of illumination light beams with different wavelengths can be emitted. For example, a lamp such as a xenon lamp, a laser diode (LD), a phosphor, and an optical filter which restricts a wavelength range may be combined with each other as necessary, so as to be used in the light source unit 20. The light source unit 20 is not limited to using the blue light source, the green light source, and the red light source, and may be configured by using a white light source emitting white light, such as a white LED, a light source emitting intermediate light between the blue light source and the green light source, or a light source emitting intermediate light between the green light source and the red light source.

The light source control unit 22 separately controls, for example, a light emission timing, a light emission amount, a wavelength range, and an optical spectrum of each light source configuring the light source unit 20 in synchronization with an imaging frame in the image sensor 48. The light source unit 20 emits illumination light under the control of the light source control unit 22. In the present embodiment, the light source unit 20 emits white light formed of R light emitted from the red light source, G light emitted from the green light source, and B light emitted from the blue light source.

The illumination light emitted from the light source unit 20 is incident to a light guide 41. The light guide 41 is built into the endoscope 12 and a universal cord, and causes the illumination light to propagate to the tip end portion 12d of the endoscope 12. The universal cord is a cord connecting the endoscope 12, the light source device 14, and the processor device 16 to each other. A multi-mode fiber may be used as the light guide 41. As an example, a fiber cable having small diameters of which a core diameter is 105 μm, a clad diameter is 125 μm, and a diameter including a protection layer serving as a sheath is ϕ0.3 to 0.5 mm may be used.

The tip end portion 12d of the endoscope 12 is provided with an illumination optical system 30a and an imaging optical system 30b. The illumination optical system 30a has an illumination lens 45, and an observation target is irradiated with illumination light via the illumination lens 45. The imaging optical system 30b has an objective lens 46, a zoom lens 47, and the image sensor 48. The image sensor 48 images an observation target by using reflected light or the like (including, in addition to the reflected light, scattering light, fluorescent light emitted from the observation target, or fluorescent light due to a drug administered to the observation target) of illumination light returning from the observation target via the objective lens 46 and the zoom lens 47. The zoom lens 47 is moved by operating the zoom operation portion 13a, and enlarges or reduces the observation target which imaged by using the image sensor 48 so as to be observed.

Figure 3:
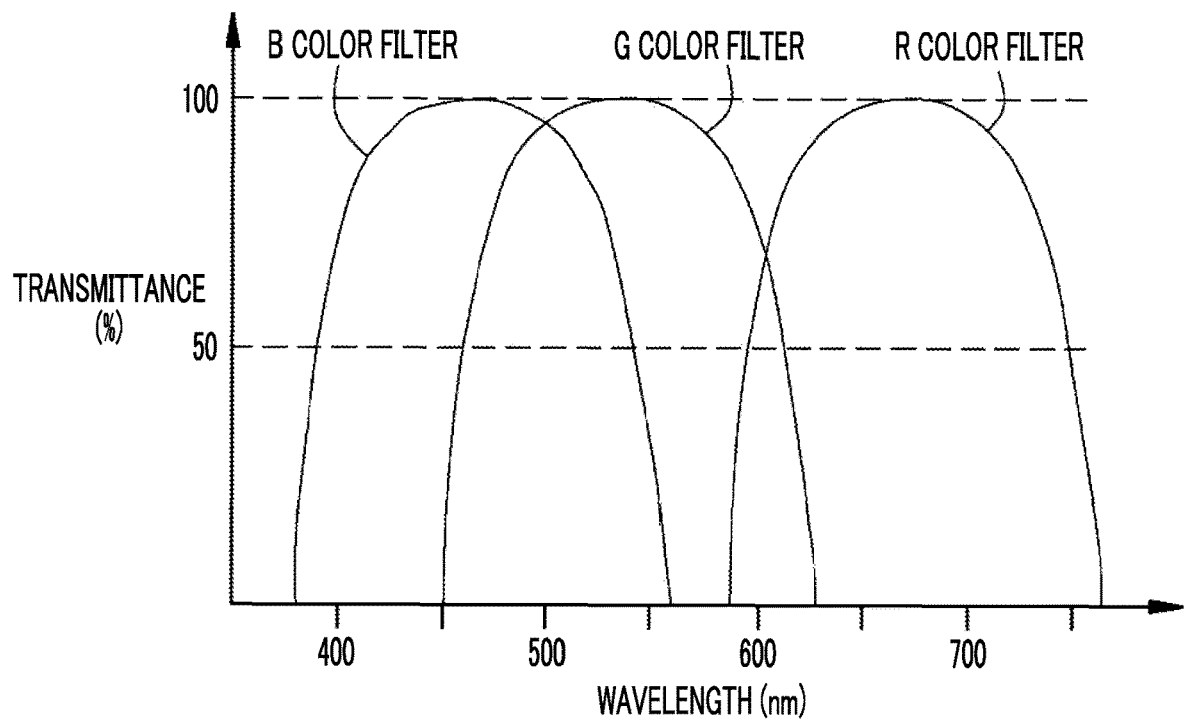
FIG. 3 is a graph illustrating spectral transmittance characteristics of color filters.

The image sensor 48 is a so-called primary color system color sensor. Thus, each pixel of the image sensor 48 has, for example, one of a red color filter (R color filter), a green color filter (G color filter), or a blue color filter (B color filter) illustrated in FIG. 3. A pixel having the R color filter is an R pixel, a pixel having the G color filter is a G pixel, and a pixel having the B color filter is a B pixel. As mentioned above, since the image sensor 48 has the pixels having three colors including the R pixel, the G pixel, and the B pixel, in a case where an observation target is imaged by using white light as illumination light, an R image 91 (refer to FIG. 5) obtained by imaging an observation target with the R pixel, a G image obtained by imaging the observation target with the G pixel, and a B image 93 (refer to FIG. 4) obtained by imaging the observation target with the B pixel are simultaneously obtained.

As described above, a color of an image through imaging in the image sensor 48 is a color of light used for the imaging. For example, light used to capture the R image 91 is R light, and the R image 91 is a red image. Similarly, the G image is a green image, and the B image 93 is a blue image. In the present embodiment, images having a plurality of colors such as the R image 91, the G image, and the B image 93 may be obtained. There is a case where a color of an image obtained through imaging is indicated by the name of a color such as red, green, or blue, and is also indicated by a wavelength range of light used for imaging.

A color filter has so-called sub-sensitivity, and, in a case where a pixel has sensitivity to light beams having a plurality of colors, plural-color images may be obtained with a single pixel. For example, in a case where an R color filter has sensitivity not only to R light but also to G light or B light, a green image or a blue image may be obtained by using an R pixel provided with the R color filter. In a case where a G color filter has sensitivity not only to G light but also to R light or B light, a red image or a blue image may be obtained by using a G pixel provided with the G color filter. In a case where a B color filter has sensitivity not only to B light but also to G light or R light, a green image or a red image may be obtained by using a B pixel provided with the B color filter. Therefore, a color of a captured image represents a color of light used for imaging, and does not depend on a pixel used for the imaging or spectral transmittance characteristics of a color filter. This is also the same for a case where a color of an image obtained through imaging is represented by using a wavelength range of light used for the imaging.

As the image sensor 48, a charge coupled device (CCD) sensor or a complementary metal oxide semiconductor (CMOS) sensor may be used. The image sensor 48 of the present embodiment is a primary color system color sensor, but a complementary color system color sensor may be used. The complementary color system color sensor has, for example, a cyan pixel provided with a cyan color filter, a magenta pixel provided with a magenta color filter, a yellow pixel provided with a yellow color filter, and a green pixel provided with a green color filter. In a case where the complementary color system color sensor is used, images obtained by using the pixels having the respective colors may be converted into the B image 93, the G image, and the R image 91 through conversion between primary colors and complementary colors. A monochrome sensor in which color filters are not provided may be used as the image sensor 48 instead of a color sensor. In this case, an observation target may be sequentially imaged by using illumination light beams having respective colors such as BGR, and thus the above-described images having the respective colors may be obtained.

The processor device 16 includes an image acquisition unit 54, an image processing unit 61, a display control unit 66, and an integral control unit 72.

The image acquisition unit 54 acquires plural-color captured images obtained by imaging an observation target by using the image sensor 48. Specifically, the image acquisition unit 54 acquires a set of the B image 93, the G image, and the R image 91 for each imaging frame. The image acquisition unit 54 includes a digital signal processor (DSP) 56, a noise reduction portion 58, and a conversion portion 59, and performs various processes on the acquired images by using the above-described elements.

The DSP 56 performs, on the acquired images, various processes such as a defect correction process, an offset process, a gain correction process, a linear matrix process, a gamma conversion process, a demosaic process, and a YC conversion process, as necessary.

The defect correction process is a process of correcting a pixel value of a pixel corresponding to a defective pixel of the image sensor 48. The offset process is a process of reducing a dark current component from an image subjected to the defect correction process, so as to set an accurate zero level. The gain correction process multiplies the imaged subjected to the offset process by a gain, so as to regulate a signal level of each image. The linear matrix process is a process of increasing color reproducibility of the image subjected to the offset process, and the gamma conversion process is a process of regulating brightness or saturation of the image subjected to the linear matrix process. The demosaic process (also referred to as an equalization process or a synchronization process) is a process of interpolating a pixel value of a missing pixel, and is performed on an image subjected to the gamma conversion process. The missing pixel is a pixel with no pixel value since pixels having other colors are disposed in the image sensor 48 for the purpose of arrangement of color filters. For example, the B image 93 is an image obtained by imaging an observation target in the B pixel, and thus a pixel at a position corresponding to the G pixel or the R pixel of the image sensor 48 does not have a pixel value. The demosaic process is a process of generating pixel values of pixels located at the G pixel and the R pixel of the image sensor 48 interpolating the B image 93. The YC conversion process is a process of converting the image subjected to the demosaic process into a luminance channel Y, and a color difference channel Cb and a color difference channel Cr.

The noise reduction portion 58 performs a noise reduction process on the luminance channel Y, the color difference channel Cb, and the color difference channel Cr by using, for example, a moving average method or a median filter method. The conversion portion 59 reconverts the luminance channel Y, the color difference channel Cb, and the color difference channel Cr subjected to the noise reduction process into images having the respective colors such as BGR.

The image processing unit 61 performs a color conversion process, a color emphasis process, and a structure emphasis process on the B image 93, the G image, and the R image 91 of a single imaging frame having undergone the various processes, so as to generate an observation image. The color conversion process is a process of performing a 3×3 matrix process, a grayscale conversion process, and a three-dimensional lookup table (LUT) process on the images having the respective colors such as BGR. The color emphasis process is a process of emphasizing a color of an image, and the structure emphasis process is a process of emphasizing, for example, tissue or a structure of an observation target such as a blood vessel or a pit pattern.

The display control unit 66 sequentially acquires observation images from the image processing unit 61, converts the acquired observation images to have a form suitable for display, and sequentially outputs and displays the observation images to and on the monitor 18. Consequently, a doctor or the like can observe an observation target by using moving observation images having shades.

The integral control unit 72 is, for example, a central processing unit (CPU), and performs integral control on the endoscope system 10, such as control of synchronization between an illumination light emission timing and an imaging frame. The integral control unit 72 includes an exposure amount control portion 73. In other words, the integral control unit 72 has a function of the exposure amount control portion 73. For example, CPU executes a program, and then the CPU functions as the image acquisition unit 54, the image processing unit 61 and display control unit 66.

The exposure amount control portion 73 acquires plural-color captured images having undergone various processes from the image acquisition unit 54, and controls an exposure amount in a case where plural-color images are obtained thereafter by using some-color images among the plural-color captured images. Specifically, the exposure amount control portion 73 acquires, for example, the R image 91, the G image, and the B image 93 of the last imaging frame from the image acquisition unit 54. All of the acquired R image 91, G image, and B image 93 are not used, an image having a specific color is selectively used from among the respective-color captured images, and, thus, for example, an exposure amount suitable to obtain the R image 91, the G image, and the B image 93 by imaging a new observation target in the next imaging frame is calculated.

The exposure amount control portion 73 inputs the calculated exposure amount to the light source control unit 22. The light source control unit 22 controls amounts of the R light, the G light, and the B light by using the exposure amounts which are input from the exposure amount control portion 73. In the present embodiment, since an exposure time of the image sensor 48 is constant, the exposure amount control portion 73 controls exposure amounts in a case where the R image 91, the G image, and the B image 93 are acquired by controlling amounts of the R light, the G light, and the B light via the light source control unit 22 as described above.

In the present embodiment, the exposure amount control portion 73 controls an exposure amount as described above by using a color captured image in which a change of a pixel value is smallest in a case where an angle of view is changed among the plural-color captured images acquired from the image acquisition unit 54. The case where an angle of view is changed is a case where an observation target is enlarged or reduced by operating the zoom operation portion 13*a*. The change of a pixel value being smallest in a case where an angle of view is changed indicates that a change ratio of a pixel value of a focused pixel to an angle of view is the minimum, or a change ratio of a statistical value such as an average value or a median value of pixel values of a focused region (including a case of all regions) to an angle of view is the minimum.

Figure 4:
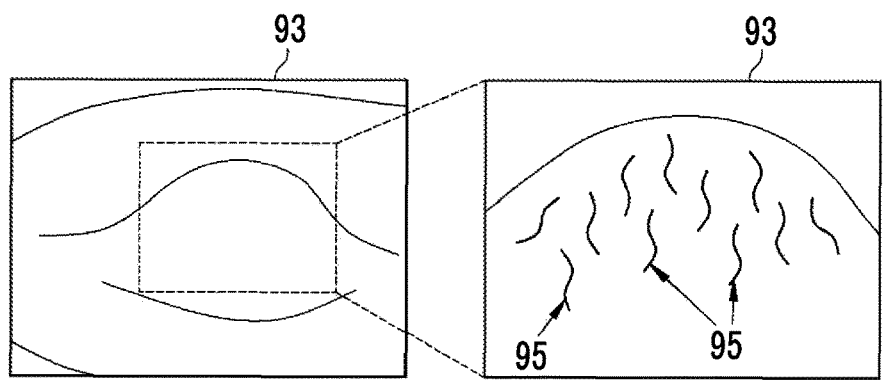
FIG. 4 is a schematic diagram of a B image when being enlarged and when not being enlarged.

For example, as illustrated in FIG. 4, the B image 93 is a color captured image in which blood vessels 95 (so-called superficial blood vessels) appear most favorably in a case where the observation target is enlarged (hereinafter, referred to as when being enlarged) among the R image 91, the G image, and the B image 93. The blood vessel 95 appearing favorably in the B image 93 is a relatively thin blood vessel, and thus does not appear much in a case where an observation target is observed without being enlarged (hereinafter, referred to as when not being enlarged). In other words, the B image 93 has a small average pixel value since the number of blood vessels 95 appearing darkly when being enlarged is large, but has a large average pixel value since the blood vessels 95 do not appear much when not being enlarged. Therefore, the B image 93 is a captured image in which a change of a pixel value with respect to an angle of view is greatest among the R image 91, the G image, and the B image 93.

Figure 5:
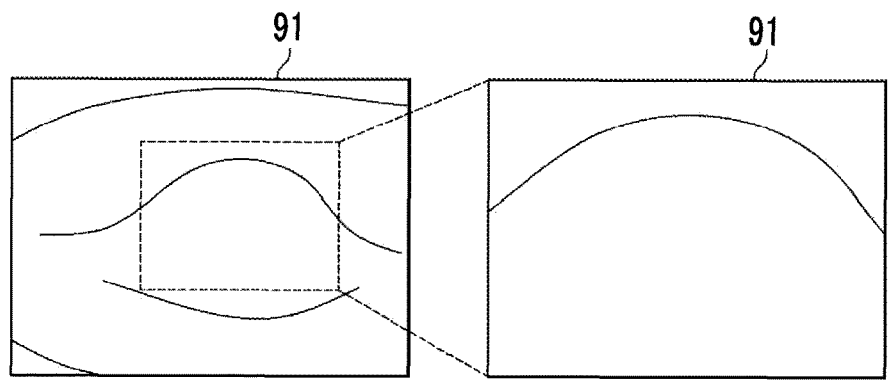
FIG. 5 is a schematic diagram of an R image when being enlarged and when not being enlarged.

On the other hand, as illustrated in FIG. 5, the R image 91 is a color captured image in which blood vessels (including the blood vessels 95) hardly appears regardless of an angle of view. In other words, in a case where the R image 91 is compared with the B image 93 and the G image, an average pixel value is great when being enlarged and when not being enlarged, and there is no great difference between average pixel values when being enlarged and when not being enlarged. Therefore, the R image 91 is a captured image in which a change of a pixel value with respect to an angle of view is smallest among the R image 91, the G image, and the B image 93.

Therefore, in the present embodiment, the exposure amount control portion 73 controls an exposure amount by using the R image 91 in which a change of a pixel value is smallest in a case where an angle of view is changed among plural-color captured images such as the R image 91, the G image, and the B image 93. Except for a special case where tissue or a structure which particularly appears in the G image is observed, an average pixel value of the G image shows an intermediate change of an average pixel value of the B image 93 and an average pixel value of the R image 91 with respect to a change of an angle of view.

Figure 6:
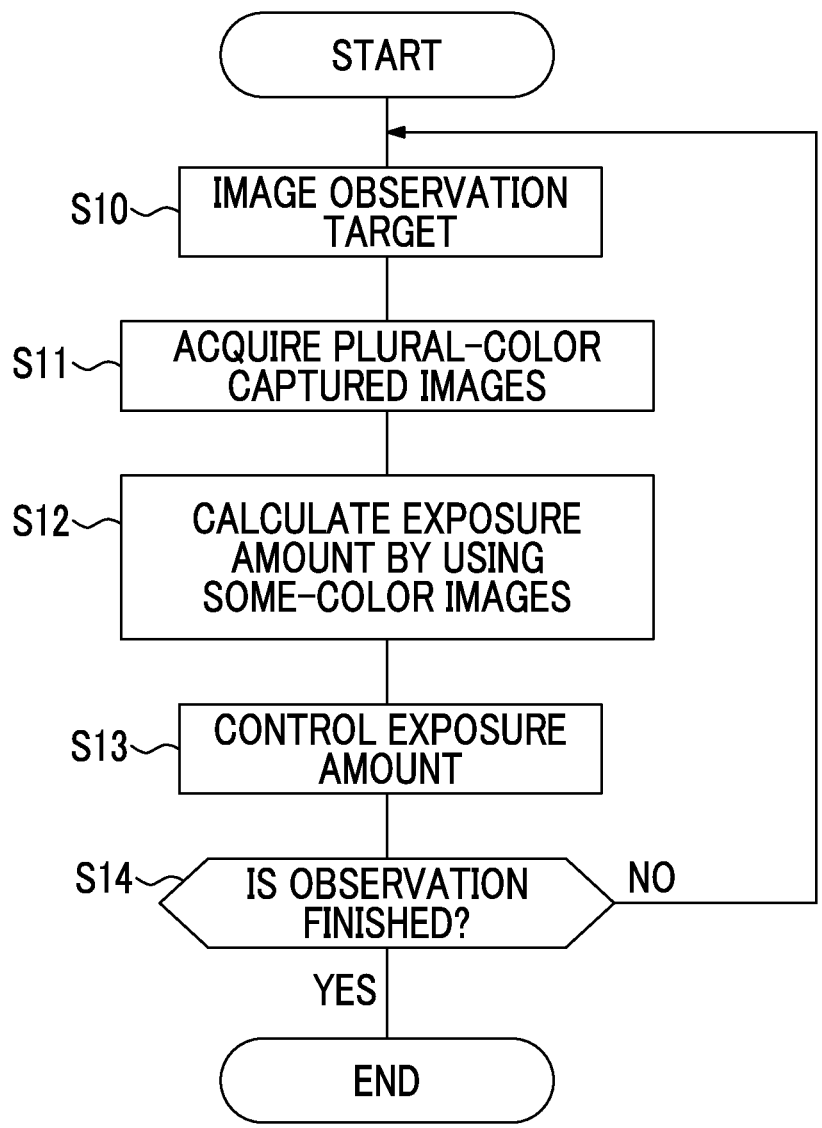
FIG. 6 is a flowchart illustrating exposure amount control in a first embodiment.

Next, a description will be made of a series of flows regarding adjustment of an exposure amount in the endoscope system 10 with reference to a flowchart in FIG. 6. First, an observation target is imaged by using white light as illumination light (S10), and, as a result, the image acquisition unit 54 acquires images having a plurality of colors, that is, the R image 91, the G image, and the B image 93 (S11).

In a case where the image acquisition unit 54 acquires the R image 91, the G image, and the B image 93 of at least one imaging frame, the exposure amount control portion 73 calculates an exposure amount in a case where the R image 91, the G image, and the B image 93 are obtained in the next imaging frame, by using some images among the plural-color captured images (S12). Specifically, since a color captured image in which a change of a pixel value is smallest in a case where an angle of view is changed is the R image 91, the exposure amount control portion 73 calculates an exposure amount by using the R image 91.

In a case where the exposure amount is calculated, the exposure amount control portion 73 controls an exposure amount in the next imaging frame by using the calculated exposure amount (S13). Specifically, the exposure amount control portion 73 inputs the calculated exposure amount to the light source control unit 22. Consequently, the light source control unit 22 adjusts an amount of the white light which is illumination light by using the exposure amount calculated by the exposure amount control portion 73. The endoscope system 10 repeatedly performs the operations (S10 to S13) until observation is finished, so that the observation target can be imaged at substantially appropriate brightness at all times.

As described above, the endoscope system 10 acquires the R image 91, the G image, and the B image 93, and generates and displays an observation image by using the acquired R image 91, G image, and B image. However, in an endoscope system of the related art, an exposure amount is controlled by using an observation image, but, in the endoscope system 10, an exposure amount is controlled by using some-color captured images among the plural-color captured images.

In a case where an exposure amount is controlled by using an observation image as in the endoscope system of the related art, even if an exposure amount to be set on the basis of an appearing state of a blood vessel appearing more darkly than the mucous membrane varies but an observation target is imaged at approximately constant brightness, flickering may occur in brightness of an observation image displayed on the monitor 18 depending on situations such as an appearing state of a blood vessel. In contrast, the endoscope system 10 controls an exposure amount by using only a captured image which does not depend on situations such as an appearing state of a blood vessel among plural-color captured images such as the R image 91, the G image, and the B image 93, instead of using an observation image for control of an exposure amount without depending on situations such as an appearing state of a blood vessel. Thus, it is possible to continuously image an observation target at constant brightness with higher accuracy than in the related art. Therefore, it is possible to reduce flickering in an observation image.

In the first embodiment, the exposure amount control portion 73 calculates an exposure amount by using an image in which a change of a pixel value is smallest in a case where an angle of view is changed among the plural-color captured images acquired from the image acquisition unit 54, and controls an exposure amount in the next imaging frame, but this is also the same for cases other than a case where the plural-color captured images are the R image 91, the G image, and the B image 93. In other words, in a case of using a complementary color system image sensor, a color of a captured image to be used for control of an exposure amount may also be selected according to an identical criterion in a case where an image sensor including color filters having different colors is used.

In the first embodiment, since white light is used illumination light, three-color captured images such as the R image 91, the G image, and the B image 93 are acquired, and a captured image used to control an exposure amount may be selected from the three-color captured images, but, in a case where only two-color captured images are obtained by using illumination light other than white light, or in a case where four-color or more captured images are obtained, an exposure amount can also be automatically adjusted in the same manner as in the first embodiment.

In the first embodiment, an image in which a change of a pixel value is smallest in a case where an angle of view is changed is used for control of an exposure amount among the plural-color captured images, but, alternatively, a color captured image in which the smallest light absorption occurs in blood (generally, hemoglobin) may be used for control of an exposure amount among the plural-color captured images. This is because, as in the first embodiment, an image of tissue or a structure including a lot of blood, such as a blood vessel, may cause an error in control of an exposure amount.

Figure 7:
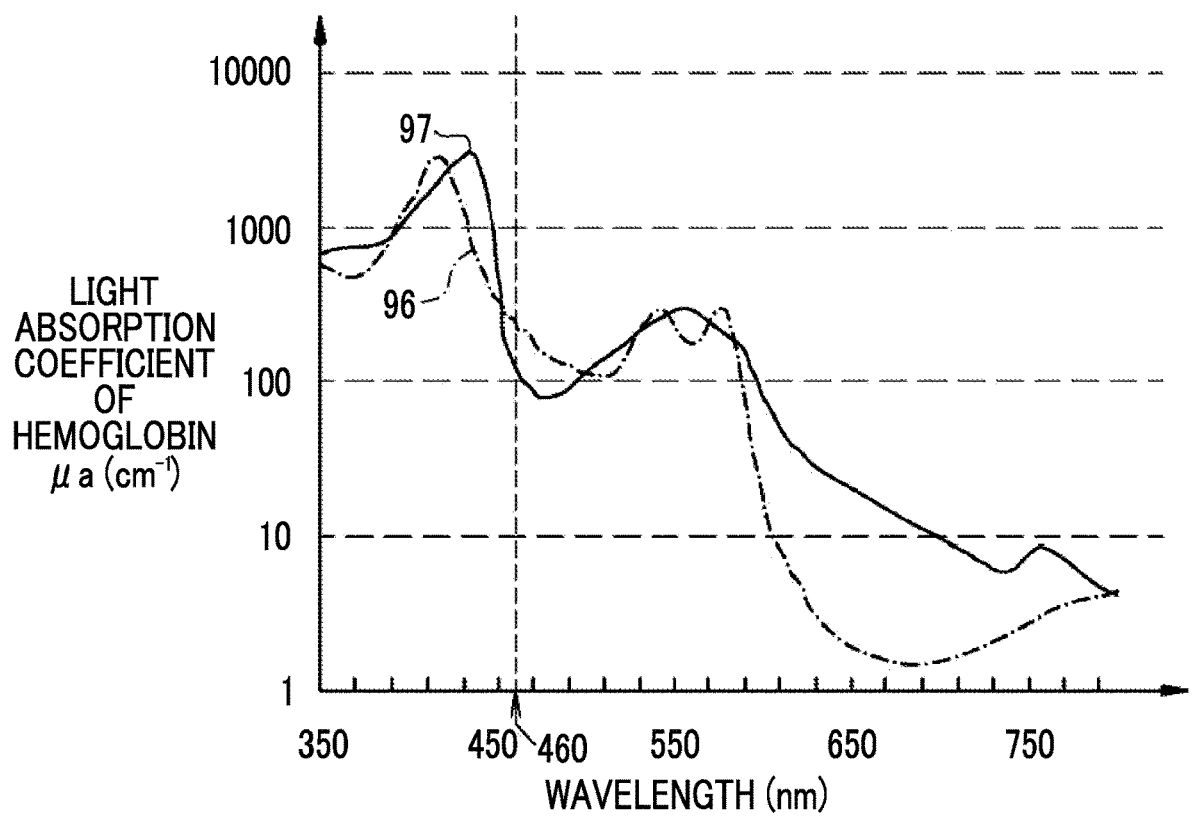
FIG. 7 is a graph illustrating a light absorption coefficient of hemoglobin.

As illustrated in FIG. 7, both of oxygenated hemoglobin 96 and reduced hemoglobin 97 have a great light absorption coefficient in a wavelength range of below about 460 nm, and thus great light absorption occurs in blood. On the other hand, light absorption coefficients of the oxygenated hemoglobin 96 and the reduced hemoglobin 97 are smaller in a wavelength range of about 460 nm or more and about 700 nm or less than in the wavelength range of below about 460 nm, and thus small light absorption occurs in blood. Therefore, a captured image (that is, a color captured image in which a wavelength range is about 460 nm or more and about 700 nm or less) obtained by imaging an observation target by using color light of which the wavelength range is about 460 nm or more and about 700 nm or less may be used for control of an exposure amount. In a case where there are a plurality of captured images obtained by imaging an observation target by using light of which the wavelength range is about 460 nm or more and about 700 nm or less, a captured image obtained by imaging the observation target by using a longer wavelength range is preferably used for control of an exposure amount. As can be seen from FIG. 7, as a wavelength becomes longer, light absorption coefficients of the oxygenated hemoglobin 96 and the reduced hemoglobin 97 become smaller, and, since a difference between the light absorption coefficients of the oxygenated hemoglobin 96 and the reduced hemoglobin 97 is small, and, as a result, light is not absorbed by blood much, and thus scarcely depends on a mixture ratio between the oxygenated hemoglobin 96 and the reduced hemoglobin 97.

As mentioned above, even in a case where a color captured image in which small light absorption occurs in blood is used for control of an exposure amount among plural-color captured images, in the same manner as in the first embodiment, in a case where the three-color captured images such as the R image 91, the G image, and the B image 93 are acquired, a captured image used for control of an exposure amount is the R image 91 in the same manner as in the first embodiment. However, in a case where a complementary color system image sensor is used, an exposure amount may be controlled with higher accuracy by using a color captured image in which small light absorption occurs in blood for control of an exposure amount among plural-color captured images.

In the first embodiment, an image in which a change of a pixel value is smallest in a case where an angle of view is changed is used for control of an exposure amount among the plural-color captured images, but, alternatively, a color captured image in which the smallest light absorption occurs in a yellow pigment may be used for control of an exposure amount among plural-color captured images. The yellow pigment is, for example, bilirubin, stercobilin, or the like. For example, in observation of the lower gastrointestinal tract such as the large intestine, there are cases in which an adhesion state of the mucous including a yellow pigment causes an error in controlling an exposure amount.

Figure 8:
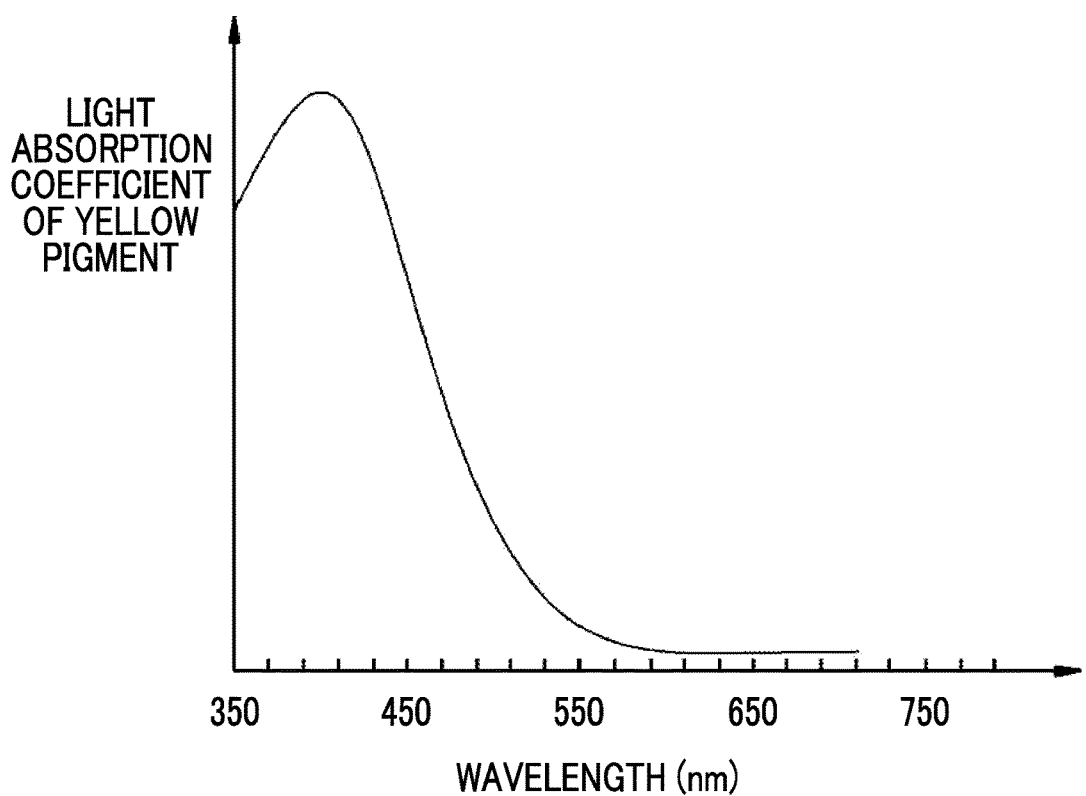
FIG. 8 is a graph illustrating a light absorption coefficient of a yellow pigment.

As illustrated in FIG. 8, a light absorption coefficient of a yellow pigment is large in a wavelength range of below about 525 nm, and is smaller in a wavelength range of about 525 nm or more and about 700 nm or less than in the wavelength range of below about 525 nm. Therefore, a captured image (that is, a color captured image in which a wavelength range is about 525 nm or more and about 700 nm or less) obtained by imaging an observation target by using light of which the wavelength range is about 525 nm or more and about 700 nm or less may be used for control of an exposure amount among plural-color captured images. As mentioned above, in a case where an exposure amount is controlled by using a color captured image in which the wavelength range is about 525 nm or more and about 700 nm or less, it is possible to control an exposure amount with high accuracy regardless of an adhesion state of the mucous including a yellow pigment in observation of the lower gastrointestinal tract such as the large intestine.

Among plural-color captured images, not only a color captured image in which the smallest light absorption occurs in blood (generally, hemoglobin) or a yellow pigment but also a color captured image in which the smallest light absorption occurs in any pigment (for example, a blue pigment) used for endoscope observation may be used for control of an exposure amount.

In the first embodiment, the exposure amount control portion 73 controls an amount of illumination light, but the exposure amount control portion 73 may control a wavelength range of illumination light or an optical spectrum of illumination light in addition to an amount of illumination light (an amount of the entire illumination light or an amount of part of the illumination light). In other words, the exposure amount control portion 73 may control an exposure amount by setting an amount, a wavelength range, or an optical spectrum of illumination light. For example, in a case where the light source unit 20 includes light sources emitting other color light beams in addition to the red light source, the green light source, and the blue light source, a wavelength range or an optical spectrum of illumination light may be controlled by adjusting a combination of lighted light sources or a light amount ratio. This is also the same for a case of using an optical filter. Of course, the exposure amount control portion 73 may control an exposure amount by simultaneously adjusting a combination of one or more of an amount, a wavelength range, and an optical spectrum of illumination light.

In the first embodiment, an exposure time of the image sensor 48 is constant, and the exposure amount control portion 73 controls an exposure amount by adjusting an amount of illumination light, but the exposure amount control portion 73 may control an exposure amount by setting an exposure time of the image sensor 48. For example, an exposure time of the image sensor 48 may be set to be long instead of increasing an amount of illumination light. The exposure amount control portion 73 may control an exposure amount by setting both of an amount, a wavelength range, or an optical spectrum of illumination light and an exposure time of the image sensor 48.

In the first embodiment, an exposure amount is controlled by selectively using the R image 91 and without using the G image and the B image 93 among three-color captured images such as the R image 91, the G image, and the B image 93, but the G image and the B image 93 may be used in addition to the R image 91. For example, the exposure amount control portion 73 may use plural-color captured images which are weighted for control of an exposure amount, and may control an exposure amount by setting weights of some-color images of plural-color images to be larger than those of the other-color images.

More specifically, in a case where a weighting factor of the R image 91 is indicated by Ar, a weighting factor of the G image is indicated by Ag, and a weighting factor of the B image 93 is indicated by Ab, the exposure amount control portion 73 sets the weighting factor Ar of the R image 91 to be the maximum among the weighting factors Ar, Ag, and Ab, so as to generate a combined image. An exposure amount in the next imaging frame may be calculated by using an average pixel value of the generated combined image. In a case where results of weighting the R image 91, the G image, and the B image 93 are used for control of an exposure amount, in the same manner as in the first embodiment, it is possible to control an exposure amount with higher accuracy than in the endoscope system of the related art. The reason is that this is substantially the same as a case of controlling an exposure amount by using the R image 91. The weighting factors preferably have a relationship of Ar>Ag and Ar>Ab. The weighting factors further preferably have a relationship of Ar>Ag>Ab.

In the modification example, a combined image obtained by combining the R image 91, the G image, and the B image 93 which are weighted with each other is used for control of an exposure amount, but, instead of combining the plural-color captured images with each other, a result of weighting an exposure amount which is calculated by using each color captured image may be used as an exposure amount in the next imaging frame. For example, a weighted average value is calculated by multiplying an exposure amount Er in the next imaging frame calculated by using the R image 91, an exposure amount Eg in the next imaging frame calculated by using the G image, and an exposure amount Eb in the next imaging frame calculated by using the B image 93, by the weighting factors Ar, Ag, and Ab. An exposure amount is controlled by using the weighted average value as an exposure amount in the next imaging frame. Also in this case, in the substantially same manner as in the first embodiment, it is possible to control an exposure amount with higher accuracy than in the endoscope system of the related art. The reason is that this is substantially the same as a case of controlling an exposure amount by using the R image 91.

Second Embodiment

Figure 9:
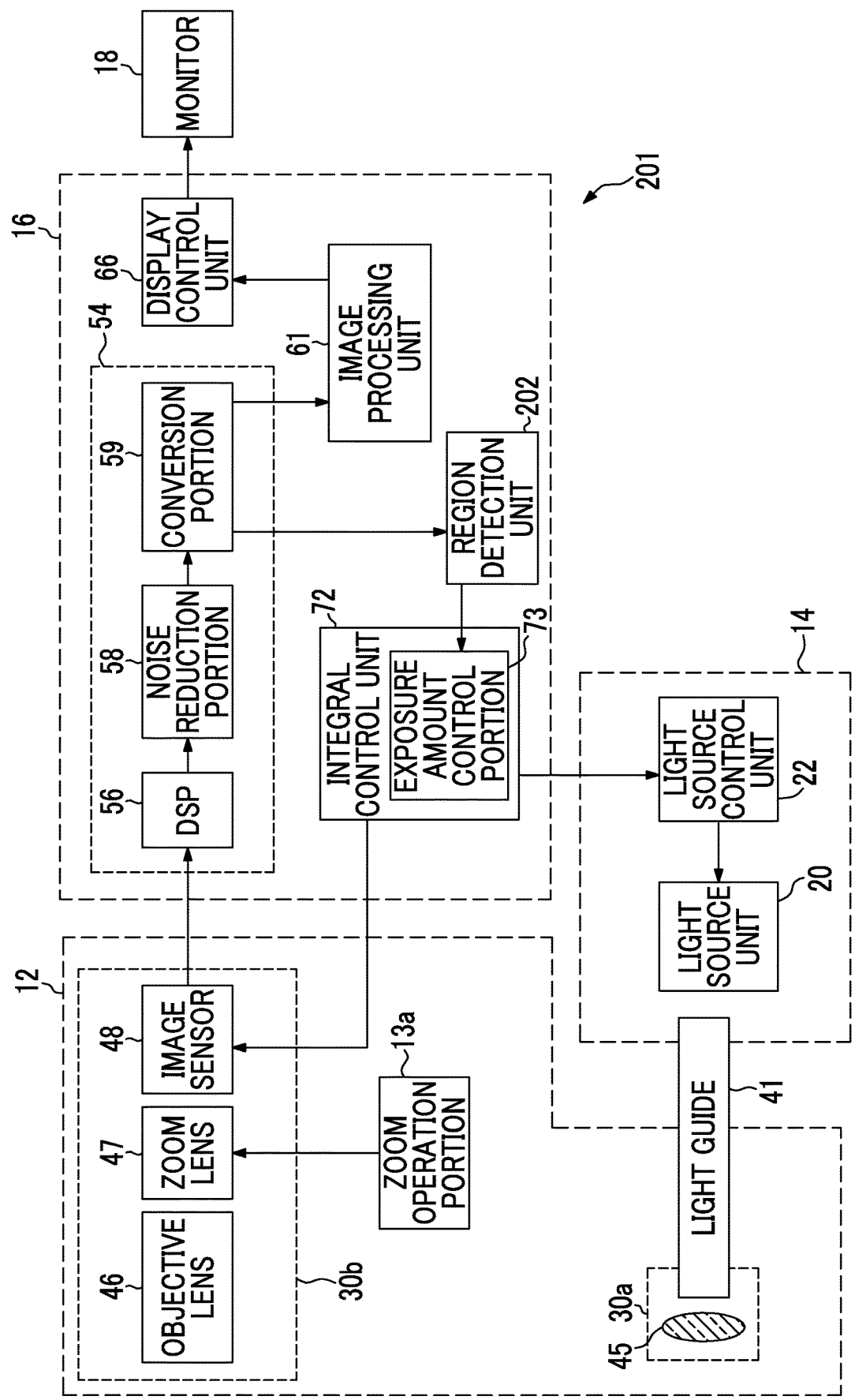
FIG. 9 is a block diagram of an endoscope system in a second embodiment.

In the first embodiment, control accuracy of an exposure amount is improved by using some-color captured images among plural-color captured images, but, for example, as in an endoscope system 201 illustrated in FIG. 9, a region detection unit 202 is provided in the processor device 16, and thus it is possible to control an exposure amount with higher accuracy.

The region detection unit 202 detects a region used for control of an exposure amount from at least a color captured image used for the exposure amount control portion 73 to control an exposure amount among plural-color captured images acquired from the image acquisition unit 54 by the exposure amount control portion 73. The region (hereinafter, referred to as a use region) used for control of an exposure amount is a region excluding a portion reducing the accuracy of exposure amount control, such as a region (hereinafter, referred to as a blood vessel region) in which a blood vessel is present. More specifically, the portion used for control of an exposure amount is an aggregate of regions formed of only the observation target mucous membrane.

For example, in a case where the exposure amount control portion 73 uses the R image 91 for control of an exposure amount, the region detection unit 202 detects a blood vessel region from at least the R image 91, and designates at least one of regions excluded from the detected blood vessel region as a use region. For example, CPU executes a program, and then the CPU functions as the region detection unit 202.

The exposure amount control portion 73 controls an exposure amount by using only pixel values of the use region detected by the region detection unit 202. In the above-described way, since a color captured image appropriate for control of an exposure amount, such as the R image 91, is used, and then an exposure amount is controlled by excluding the blood vessel region causing an error, it is possible to control an exposure amount with further higher accuracy than in the first embodiment.

Third Embodiment

In the first embodiment, the R image 91 is selectively used, and an exposure amount is controlled, under the criterion that a change of a pixel value is smallest in a case where an angle of view is changed among plural-color captured images. Thus, in the first embodiment, in a case where the endoscope system 10 acquires three-color captured images such as the R image 91, the G image, and the B image 93, the use of the R image 91 is automatically determined in advance. However, instead of determining a color captured image to be used for control of an exposure amount in advance as in the first embodiment, a captured image to be used for control of an exposure amount may be selected more flexibly according to an observation situation or an observation part.

Figure 10:
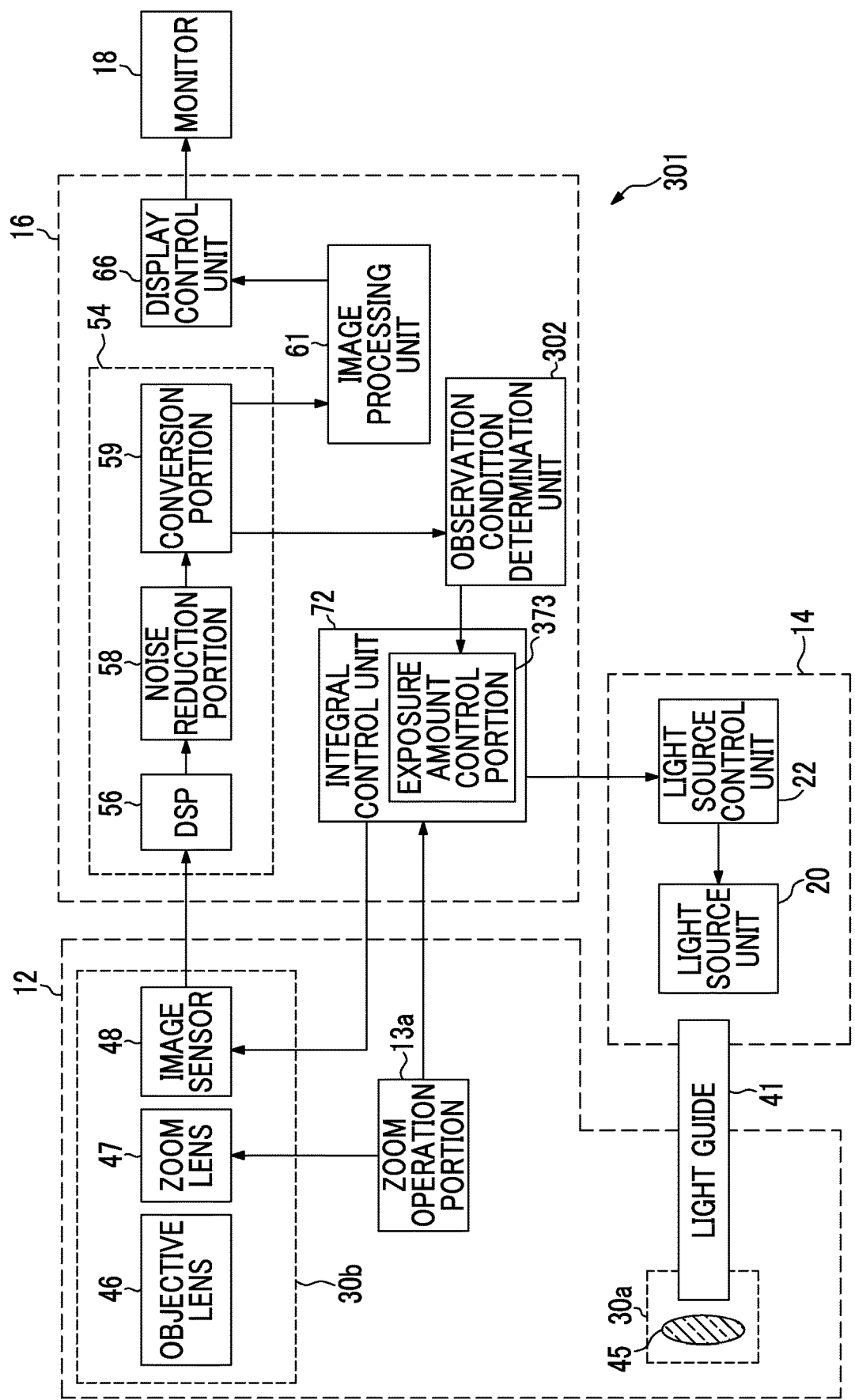
FIG. 10 is a block diagram of an endoscope system in a third embodiment.

In this case, for example, as in an endoscope system 301 illustrated in FIG. 10, an observation condition determination unit 302 is provided in the processor device 16. The observation condition determination unit 302 determines an observation condition by using one or more of plural-color images acquired from the image acquisition unit 54 by an exposure amount control portion 373. The exposure amount control portion 373 selects a captured image to be used for control of an exposure amount from among plural-color captured images by using the observation condition determined by the observation condition determination unit 302. For example, CPU executes a program, and then the CPU functions as the observation condition determination unit 302.

The observation condition is, for example, an observation distance or an observation part. The observation distance may be determined on the basis of the brightness of the mucous membrane or the like in a captured image, or an operation state (the extent of zooming) of the zoom operation portion 13a.

The observation part may be determined on the basis of the brightness of the mucous membrane or the like in a captured image, a thickness of a blood vessel, a density of a blood vessel, a color of the mucous membrane, or a contrast of a blood vessel or the like to the mucous membrane. For example, in a case where the observation part is the esophagus, there are a lot of superficial blood vessels locally present near the surface of the mucous membrane, and, in a case where the observation part is the stomach, a lot of middle-deep blood vessels which are located at a deeper position than the superficial blood vessels under the mucous membrane may be observed, for example, in the G image. Thus, the observation part may be determined on the basis of a blood vessel appearing in a captured image. The presence or absence of a blood vessel and a thickness of a blood vessel are determined through, for example, frequency analysis.

Figure 11:
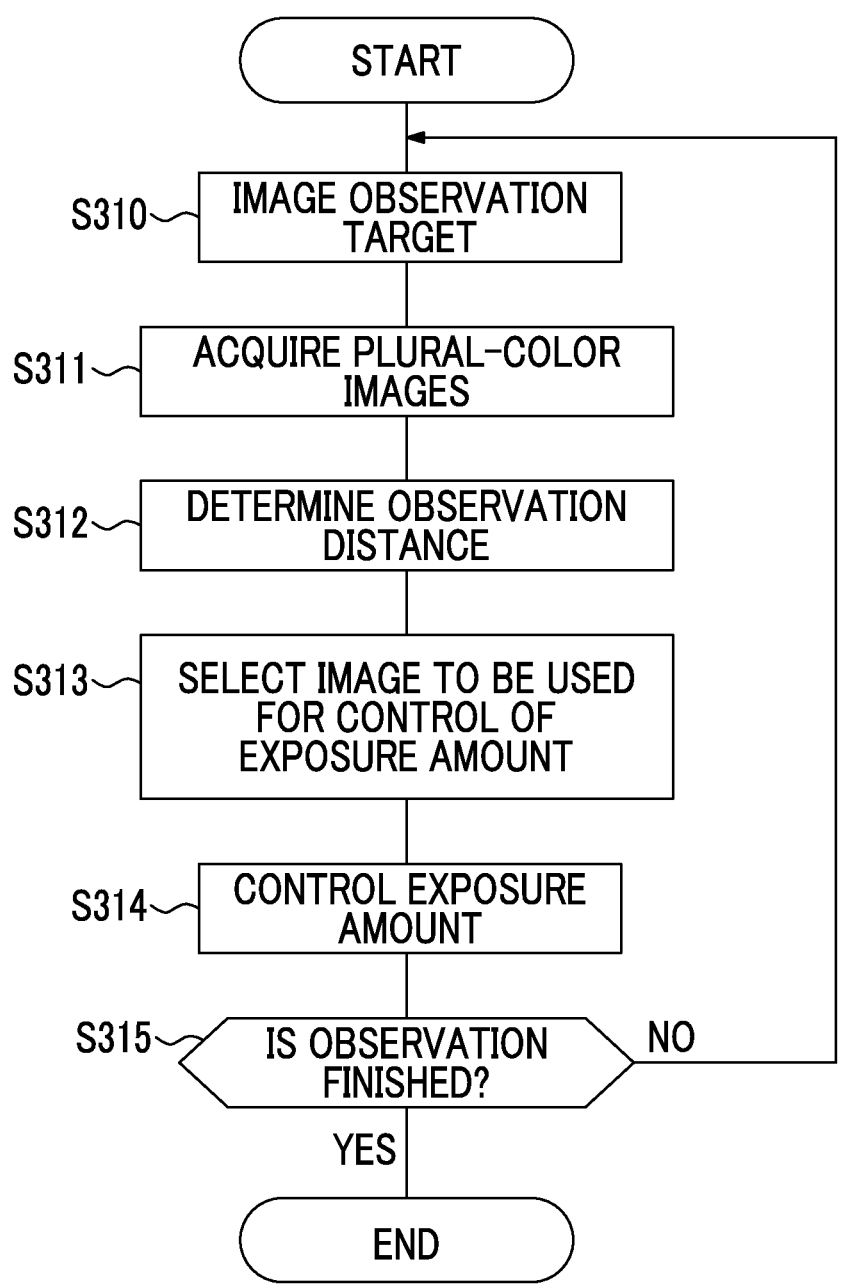
FIG. 11 is a flowchart illustrating exposure amount control in a case where an observation distance is determined.

As illustrated in FIG. 11, in a case where the observation condition determination unit 302 determines an observation distance as an observation condition, an observation target is imaged (S310), and, in a case where the image acquisition unit 54 acquires plural-color captured images (S311), the observation condition determination unit 302 determines an observation distance by using one or more of the plural-color captured images acquired by the image acquisition unit 54 (S312). The exposure amount control portion 373 selects a captured image to be used for control of an exposure amount by using the observation distance determined by the observation condition determination unit 302 (S313). Specifically, in a case where the observation distance is long, and the observation target is imaged far away, the exposure amount control portion 373 selects a long wavelength color captured image. For example, in a case where the observation distance is short, and a lot of blood vessels 95 appear in the B image 93, the exposure amount control portion 373 selects the R image 91 or the G image in which few blood vessels 95 appear as a captured image to be used for control of an exposure amount. In a case where blood vessels also appear in the G image, the exposure amount control portion 373 selects the R image 91 as a captured image to be used for control of an exposure amount. In a case where few blood vessels 95 also appear in the B image 93, any one of the R image 91, the G image, or the B image 93 may be selected as a captured image to be used for control of an exposure amount.

In the above-described way, in a case where a color captured image to be used for control of an exposure amount is selected from among plural-color images, the exposure amount control portion 373 controls an exposure amount by using the selected color captured image (S314). An exposure amount control method and repeatedly performing the operations until the observation is finished (S315) are the same as in the first embodiment.

Figure 12:
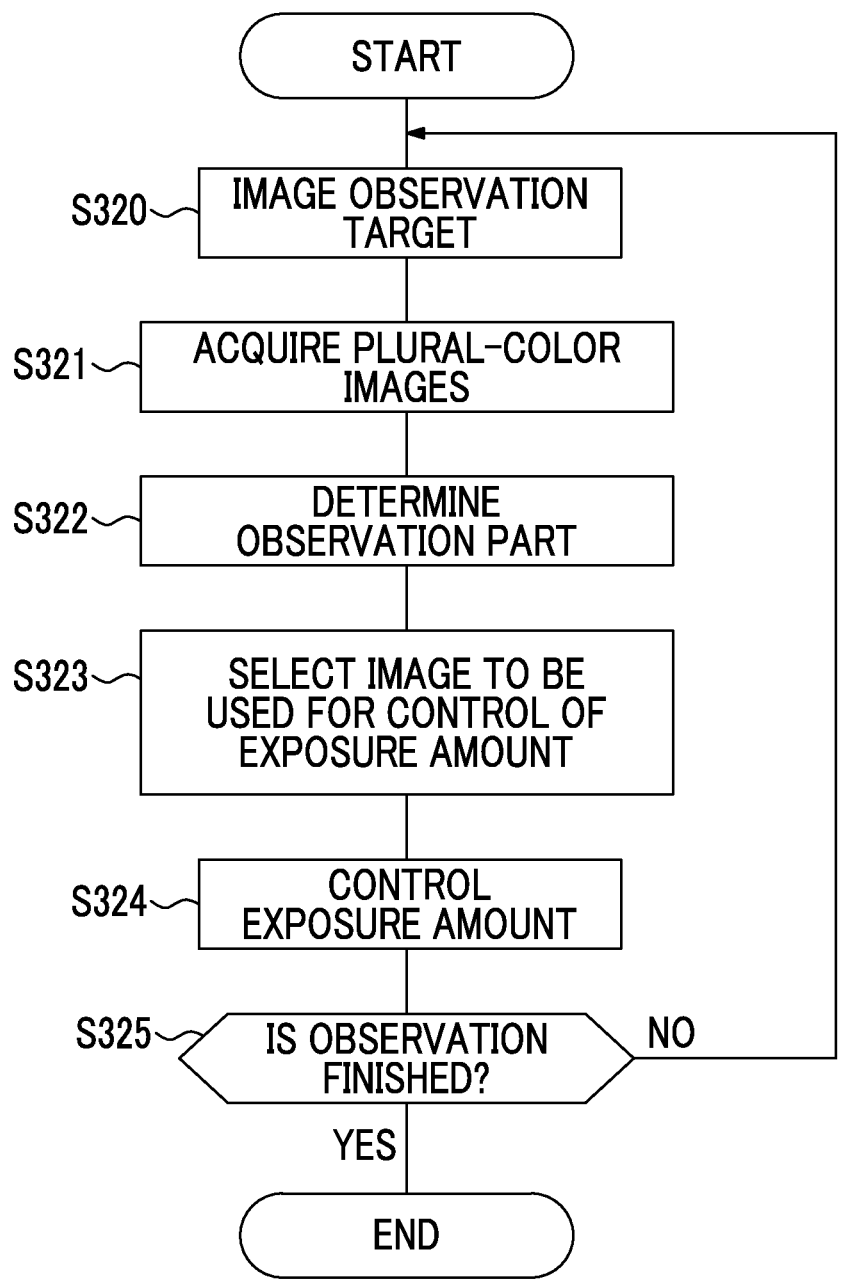
FIG. 12 is a flowchart illustrating exposure amount control in a case where an observation part is determined.

As illustrated in FIG. 12, in a case where the observation condition determination unit 302 determines an observation part as an observation condition, an observation target is imaged (S320), and, in a case where the image acquisition unit 54 acquires plural-color captured images (S321), the observation condition determination unit 302 determines an observation part by using one or more of the plural-color captured images acquired by the image acquisition unit 54 (S322). The exposure amount control portion 373 selects a captured image to be used for control of an exposure amount by using the observation part determined by the observation condition determination unit 302 (S323). For example, in a case where the observation condition determination unit 302 determines that the observation part is the "esophagus", a lot of the blood vessels 95 appear in the B image 93, and thus the exposure amount control portion 373 excludes the B image 93, and selects the G image or the R image 91 as a captured image to be used for control of an exposure amount. In a case where the observation condition determination unit 302 determines that the observation part is the "stomach", the blood vessels 95 appear in the G image, and thus the B image 93 or the R image 91 is selected as a captured image to be used for control of an exposure amount.

In the above-described way, in a case where a color captured image to be used for control of an exposure amount is selected from among plural-color images, the exposure amount control portion 373 controls an exposure amount by using the selected color captured image (S324). An exposure amount control method and repeatedly performing the operations until the observation is finished (S325) are the same as in the case where the observation condition determination unit 302 determines an observation distance.

Figure 13:
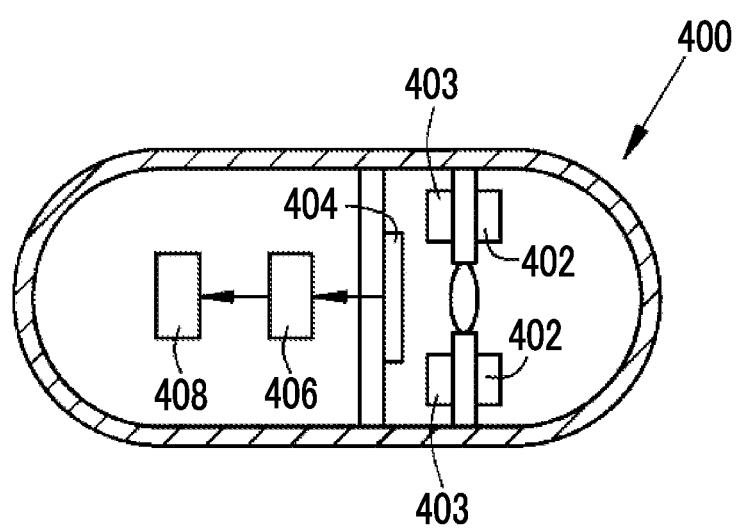
FIG. 13 is a schematic diagram of a capsule endoscope.

In the first to third embodiments, the present invention is implemented in the endoscope system in which the endoscope 12 provided with the image sensor 48 is inserted into a subject and observation is performed, but the present invention is suitable for a capsule endoscope system. As illustrated in FIG. 13, for example, a capsule endoscope system includes at least a capsule endoscope 400 and a processor device (not illustrated).

The capsule endoscope 400 includes a light source unit 402, a control unit 403, an image sensor 404, an image processing unit 406, and a transmission/reception antenna 408. The light source unit 402 corresponds to the light source unit 20. The control unit 403 functions in the same manner as the light source control unit 22, the integral control unit 72, and the exposure amount control portion 73. The control unit 403 performs communication with the processor device of the capsule endoscope system in a wireless manner by using the transmission/reception antenna 408. The processor device of the capsule endoscope system is substantially the same as the processor device 16 of the first to third embodiments, but the image processing unit 406 corresponding to the image acquisition unit 54 and the image processing unit 61 is provided in the capsule endoscope 400, and a generated observation image is transmitted to the processor device via the transmission/reception antenna 408. The image sensor 404 is configuration in the same manner as the image sensor 48.

EXPLANATION OF REFERENCES 10, 201, and 301: endoscope system
12: endoscope
12a: insertion portion
12b: operation portion
12c: curved portion
12d: tip end portion
12e: angle knob
13a: zoom operation portion
14: light source device
16: processor device
18: monitor
19: console
20 and 402: light source unit
22: light source control unit
30a: illumination optical system
30b: imaging optical system
41: light guide
45: illumination lens
46: objective lens
47: zoom lens
48 and 404: image sensor
54: image acquisition unit
56: DSP
58: noise reduction portion
59: conversion portion
61 and 406: image processing unit
66: display control unit
72: integral control unit
73 and 373: exposure amount control portion
91: R image
93: B image 95: blood vessel
96: oxygenated hemoglobin
97: reduced hemoglobin
202: region detection unit
302: observation condition determination unit
400: capsule endoscope
403: control unit
408: transmission/reception antenna

What is claimed is:

1. A processor device comprising:
an image acquisition unit that acquires plural-color images from an image sensor which images an observation target by using illumination light, wherein the plural-color images are a set of different monochrome images;
an exposure amount control portion that controls an exposure amount to be constant in a case where the image acquisition unit obtains the plural-color images, by using some-color images of the plural-color images; and
a region detection unit that detects a region to be used for control of an exposure amount from the plural-color images,
wherein the exposure amount control portion controls the exposure amount by using the region detected by the region detection unit,
wherein the exposure amount control portion controls the exposure amount by using a color image in which a change of a pixel value is smallest in a case where an angle of view is changed among the plural-color images.

2. An endoscope system comprising:
the processor device according to claim 1;
a light source unit that emits the illumination light; and
the image sensor that images the observation target by using the illumination light.

3. The endoscope system according to claim 2, further comprising:
a light source control unit that controls an amount, a wavelength range, or an optical spectrum of the illumination light emitted from the light source unit,
wherein the exposure amount control portion calculates the exposure amount in a case where the image acquisition unit obtains the plural-color images, by using some-color images of the plural-color images, outputs the calculated exposure amount to the light source control unit, and controls the exposure amount.

4. The endoscope system according to claim 2,
wherein the exposure amount control portion controls the exposure amount by using a color image in which the smallest light absorption occurs in blood among the plural-color images.

5. The endoscope system according to claim 2,
wherein the exposure amount control portion controls the exposure amount by using a color image in which a wavelength range is 460 nm or more and 700 nm or less among the plural-color images.

6. The endoscope system according to claim 3,
wherein the exposure amount control portion controls the exposure amount by using a color image in which a wavelength range is 460 nm or more and 700 nm or less among the plural-color images.

7. The endoscope system according to claim 2,
wherein the exposure amount control portion controls the exposure amount by using a color image in which the smallest light absorption occurs in a yellow pigment among the plural-color images.

8. The endoscope system according to claim 2,
wherein the exposure amount control portion controls the exposure amount by using a color image in which a wavelength range is 525 nm or more and 700 nm or less among the plural-color images.

9. The endoscope system according to claim 2,
wherein the exposure amount control portion controls the exposure amount by using a color image in which the smallest light absorption occurs in a pigment used for endoscope observation among the plural-color images.

10. The endoscope system according to claim 2,
wherein the exposure amount control portion controls the exposure amount by setting an amount, a wavelength range, or an optical spectrum of light included in the illumination light.

11. The endoscope system according to claim 2,
wherein the exposure amount control portion controls the exposure amount by setting an exposure time of the image sensor.

12. The endoscope system according to claim 2,
wherein the exposure amount control portion uses the plural-color images which are weighted for the control of the exposure amount, and controls the exposure amount by setting weights of some-color images of the plural-color images to be larger than weights of the other-color images.

13. The endoscope system according to claim 2, further comprising: an observation condition determination unit that determines an observation condition by using one or more of the plural-color images, wherein the exposure amount control portion selects an image to be used for the control of the exposure amount from among the plural-color images by using the observation condition.

14. The endoscope system according to claim 13, wherein the observation condition determination unit determines an observation distance as the observation condition.

15. The endoscope system according to claim 13, wherein the observation condition determination unit determines an observation part as the observation condition.

16. The processor device according to claim 1,
wherein the region detection unit detects a region excluding a portion reducing the accuracy of exposure amount control from the plural-color images as the region to be used for the control of the exposure amount.

17. The endoscope system according to claim 15, further comprising: a light source control unit that controls an amount, a wavelength range, or an optical spectrum of the illumination light emitted from the light source unit, wherein the exposure amount control portion calculates the exposure amount in a case where the image acquisition unit obtains the plural-color images, by using some-color images of the plural-color images, outputs the calculated exposure amount to the light source control unit, and controls the exposure amount, and wherein the region detection unit detects a region excluding a portion reducing the accuracy of exposure amount control from the plural-color images as the region to be used for the control of the exposure amount.

18. An endoscope system operation method using the endoscope system according to claim 2 comprising:
causing the light source unit to emit the illumination light;
causing the image sensor to image the observation target by using the illumination light;
causing the image acquisition unit to acquire the plural-color images obtained by imaging the observation target by using the image sensor;
causing the exposure amount control portion to control the exposure amount to be constant in a case where the image acquisition unit obtains the plural-color images, by using some-color images among the plural-color images; and causing the region detection unit to detect a region to be used for the control of the exposure amount from the plural-color images.

19. The processor device according to claim 1, wherein the plural-color images are the set of different monochrome images obtained in each imaging frame.

* * * * *